(12) United States Patent
Sinha et al.

(10) Patent No.: US 9,034,896 B2
(45) Date of Patent: *May 19, 2015

(54) N-(IMIDAZOLIDIN-2-YLIDENE)-HETERO-CYCLOPENTA[B]PYRIDINE DERIVATIVES AS MODULATORS OF ALPHA 2 ADRENERGIC RECEPTORS

(71) Applicant: Allergan, Inc., Irvine, CA (US)

(72) Inventors: Santosh C. Sinha, Ladera Ranch, CA (US); Liming Wang, Irvine, CA (US); Ken Chow, Newport Coast, CA (US); Mohammed I. Dibas, Laguna Niguel, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/257,517

(22) Filed: Apr. 21, 2014

(65) Prior Publication Data

US 2014/0228395 A1  Aug. 14, 2014

Related U.S. Application Data

(60) Continuation of application No. 13/945,825, filed on Jul. 18, 2013, now Pat. No. 8,741,921, which is a division of application No. 13/546,211, filed on Jul. 11, 2012, now Pat. No. 8,513,419.

(60) Provisional application No. 61/511,372, filed on Jul. 25, 2011.

(51) Int. Cl.
| | | |
|---|---|---|
| *C07D 471/04* | (2006.01) | |
| *C07D 491/048* | (2006.01) | |
| *C07D 513/04* | (2006.01) | |
| *C07D 491/04* | (2006.01) | |
| *C07D 498/04* | (2006.01) | |
| *B65D 25/20* | (2006.01) | |

(52) U.S. Cl.
CPC ............ *C07D 471/04* (2013.01); *C07D 491/04* (2013.01); *C07D 498/04* (2013.01); *B65D 25/205* (2013.01); *C07D 491/048* (2013.01); *C07D 513/04* (2013.01)

(58) Field of Classification Search
None
See application file for complete search history.

(56) References Cited

U.S. PATENT DOCUMENTS

| | | | |
|---|---|---|---|
| 4,166,452 | A | 9/1979 | Generales et al. |
| 4,256,108 | A | 3/1981 | Theeuwes |
| 4,265,874 | A | 5/1981 | Bonsen et al. |
| 5,677,321 | A | 10/1997 | Jeon et al. |
| 2002/0065307 | A1 | 5/2002 | Jeon et al. |

FOREIGN PATENT DOCUMENTS

| | | |
|---|---|---|
| WO | 95-16685 | 6/1995 |
| WO | 98-23612 | 6/1998 |
| WO | 98-46572 | 10/1998 |
| WO | 2011-044229 | 4/2011 |

OTHER PUBLICATIONS

Cross, LC, Rules for the Nomenclature of Organic Chemistry Section E: Sterochemistry, Pure & Appl. Chem., 1976, 11-30, 45.
Heinrich Stahl, Pharmaceutical Salts, Handbook of Pharmaceutical Salts, 2002, 329-345, International Union of Pure and Applied Chemistry, Verlag Helvetica Chemica Acta—Zürich.
Messier, Terri, High Throughput Assays of Cloned Adrenergic, Muscarinic, Neurokinin, and Neurotrophin Receptors in Living Mammalian Cells, Pharmacology & Toxicology, 1995, 308-311, 76, US.
Remingtons, Remingtons_16th, Pharmaceutical Sciences, 1980, 1-10, 16, Remingtons_16th.
Patent Cooperation Treaty, Notification of Transmittal of the International Search Report and the Written Opinion of the International Searching Authority, or the Declaration, Form PCT/ISAI220, In!. App. No. PCT/US2012/046161, Sep. 12, 2012.

*Primary Examiner* — Timothy R Rozof
(74) *Attorney, Agent, or Firm* — Barbara C. Potts

(57) ABSTRACT

The present invention relates to novel N-(imidazolidin-2-ylidene) Heterocyclopenta[b]pyridine derivatives, processes for preparing them, pharmaceutical compositions containing them and their use as pharmaceuticals.

9 Claims, No Drawings

N-(IMIDAZOLIDIN-2-YLIDENE)-HETEROCYCLOPENTA[B]PYRIDINE DERIVATIVES AS MODULATORS OF ALPHA 2 ADRENERGIC RECEPTORS

RELATED APPLICATION

This application is a continuation application of U.S. Nonprovisional patent application Ser. No. 13/945,825, filed Jul. 18, 2013, which is a divisional application of U.S. Nonprovisional patent application Ser. No. 13/546,211, filed Jul. 11, 2012, granted as U.S. Pat. No. 8,513,419, which claims the benefit of U.S. Provisional Application Ser. No. 61/511,372, filed Jul. 25, 2011, all of which are incorporated here by reference in their entirety.

FIELD OF THE INVENTION

The present invention relates to novel N-(imidazolidin-2-ylidene)-heterocyclopenta[b]pyridine derivatives, as alpha 2 adrenergic modulators. Alpha 2 adrenergic receptors have been characterized by molecular and pharmacological methods which include alpha 1A, alpha 1B, alpha 2A, alpha 2B and alpha 2C. Activation of these alpha receptors evokes physiological responses. Adrenergic modulators described in this invention activate alpha 2 receptors and have useful therapeutic actions.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine. Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. Functional differences between $\alpha_1$ and $\alpha_2$ receptors have been recognized, and compounds which exhibit selective binding between these two subtypes have been developed.

SUMMARY OF THE INVENTION

The present invention relates to novel N-(imidazolidin-2-ylidene) heterocyclopental[b]pyridine derivatives, as alpha 2 adrenergic modulators. These novel compounds will be useful for the treatment of mammals, including humans, with a range of conditions and diseases that are alleviated by alpha 2A, 2B, 2C activation, including but not limited to treating glaucoma, elevated intraocular pressure, ischemic neuropathies, optic neuropathy, pain, visceral pain, corneal pain, headache pain, migraine, cancer pain, back pain, irritable bowel syndrome pain, muscle pain and pain associated with diabetic neuropathy, the treatment of diabetic retinopathy, other retinal degenerative conditions, stroke, cognitive deficits, neuropsychiatric conditions, drug dependence and addiction, withdrawal symptoms, obsessive-compulsive disorders, obesity, insulin resistance, stress-related conditions, diarrhea, diuresis, nasal congestion, spasticity, attention deficit disorder, psychoses, anxiety, depression, autoimmune disease, Crohn's disease, gastritis, Alzheimer's, Parkinson's ALS, neurodegenerative diseases, retinal neuroprotection, skin conditions, skin diseases, rosacea, sunburn, psoriasis, acne rosacea, menopause-associated hot flashes, hot flashes resulting from orchiectomyatopic dermatitis, photoaging, seborrheic dermatitis, acne, allergic dermatitis, redness of the skin, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, erythema of the skin, cutaneous hyperactivity with dilation of blood vessels of the skin, Lyell's syndrome, Stevens-Johnson syndrome, erythema multiforme minor, erythema multiforme major and/or other inflammatory skin diseases, age related macular degeneration, wet macular degeneration, dry macular degeneration, geographic atrophy, diabetic retinopathy, diabetic macular edema, tumors, wound healing, inflammation and retinal vein occlusion, enhancing vision in patients with vision loss from conditions including glaucoma, retinitis pigmentosa and neuritis secondary to multiple sclerosis.

In one aspect, the invention therefore provides a compound of Formula I, its enantiomers, diastereoisomers, hydrates, solvates, crystal forms and individual isomers, tautomers or a pharmaceutically acceptable salt thereof,

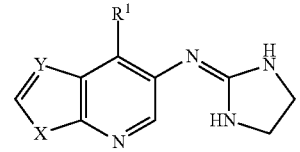

Formula I wherein:
$R^1$ is hydrogen, $C_{1-8}$ alkyl or halogen;
Y is CH or N;
X is O, S, NR; and
R is hydrogen or $C_{1-3}$ alkyl.

In another aspect, the invention provides a compound having Formula I wherein:
$R^1$ is hydrogen, methyl, bromine or chlorine;
Y is CH or N;
X is O, S, NR; and
R is hydrogen or methyl.

In another aspect, the invention provides a compound having Formula I wherein:
$R^1$ is hydrogen;
Y is CH;
X is O, NR; and
R is hydrogen or methyl.

In another aspect, the invention provides a compound having Formula I wherein:
$R^1$ is hydrogen;
Y is CH;
X is NR; and
R is hydrogen or methyl.

In another aspect, the invention provides a compound having Formula I wherein:
$R^1$ is methyl;
Y is CH;
X is NR; and
R is methyl.

In another aspect, the invention provides a compound having Formula I wherein:
$R^1$ is bromine or chlorine;
Y is CH;
X is NR; and
R is hydrogen.

In another aspect, the invention provides a compound having Formula I wherein:
$R^1$ is hydrogen;
Y is N;
X is O, S, NR; and
R is hydrogen or methyl.

In another aspect, the invention provides a compound having Formula I wherein:
$R^1$ is hydrogen;
Y is N;
X is S, NR; and
R is hydrogen or methyl.

In another aspect, the invention provides a compound having Formula I wherein:
$R^1$ is hydrogen;
Y is N; and
X is S.

In another aspect, the invention provides a compound having Formula I wherein:
$R^1$ is hydrogen;
Y is N;
X is NR; and
R is hydrogen or methyl.

The term "alkyl" as used herein, is defined as including a saturated monovalent hydrocarbon moiety having straight or branched moieties or combinations thereof and containing 1-8 carbon atoms, preferably 1-6 carbon atoms and more preferably 1-4 carbon atoms. Alkyl moieties can optionally be substituted by amino groups, halogens or one methylene (—$CH_2$—) can be replaced by carbonyl, NH, carboxyl or by oxygen.

The term "H" as used herein refers to a hydrogen atom.
The term "O" as used herein refers to an oxygen atom.
The term "S" as used herein refers to a sulfur atom.
The term "N" as used herein refers to a nitrogen atom.
The term "amino" as used herein refers to a group of formula —$NH_2$.
The term "halogen", as used herein refers to an atom of chlorine, bromine, iodine or fluorine.
The term "carbonyl" as used herein refers to a group of formula —C=O.
The term "carboxyl", as used herein refers to a group of formula —C(O)O—.

Compounds of the invention are:
N-(imidazolidin-2-ylidene)-1H-pyrrolo[2,3-b]pyridin-5-amine;
N-(imidazolidin-2-ylidene)-4-methyl-1H-pyrrolo[2,3-b]pyridin-5-amine;
4-Chloro-N-(imidazolidin-2-ylidene)-1H-pyrrolo[2,3-b]pyridin-5-amine;
4-Bromo-N-(imidazolidin-2-ylidene)-1H-pyrrolo[2,3-b]pyridin-5-amine;
N-(imidazolidin-2-ylidene)-1-methyl-1H-pyrrolo[2,3-b]pyridin-5-amine;
N-(imidazolidin-2-ylidene)furo[2,3-b]pyridin-5-amine;
N-(imidazolidin-2-ylidene)-3H-imidazo[4,5-b]pyridin-6-amine;
N-(imidazolidin-2-ylidene)thiazolo[5,4-b]pyridin-6-amine.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

As used herein, "tautomer" refers to the migration of protons between adjacent single and double bonds. The tautomerization process is reversible. Compounds described herein can undergo any possible tautomerization that is within the physical characteristics of the compound.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, a hydrohalic acid, such as hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahl & Camille G. Wermuth (Eds), Verlag Helvetica Chimica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back of the eye, front of the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

An ophthalmically acceptable pharmaceutical composition is one that can be administered topically to the eye of a subject in need thereof. Comfort to the subject being administered the composition should be maximized, but other considerations, such as drug stability, may necessitate a pharmaceutical composition that provides less than optimal comfort. In such a case, the composition should be formulated such that it is tolerable to a subject being administered the composition topically.

The claimed pharmaceutical composition can be administered topically in the form of solutions or suspensions, ointments, gels, creams, etc. A "pharmaceutically acceptable excipient" is one that is compatible with the active ingredient of the composition and not harmful to the subject being administered the pharmaceutical composition. Solutions for ophthalmic application are often prepared using physiological saline as a major vehicle. Other vehicles include polyvinyl alcohol, povidone, hydroxypropyl methyl cellulose, poloxamers, carboxymethyl cellulose, hydroxyethyl cellulose, and purified water. Examples of useful excipients also include preservatives, buffers, other pH adjustors, tonicity adjustors, surfactants, antioxidants, and chelating agents.

Useful preservatives include benzalkonium chloride, chlorobutanol, thimerosal, phenylmercuric acetate and phenylmercuric nitrate. Examples of buffers include phosphate, borate, sulfate, acetate, and citrate buffers. Acids or bases may be used to adjust the pH of the compositions as needed. Examples of tonicity agents include glycerin, mannitol, sodium chloride and potassium chloride. Useful surfactants include, for example, Tween 80. Examples of ophthalmically acceptable antioxidants include sodium metabisulfite, sodium thiosulfate, acetylcysteine, butylated hydroxyanisole and butylated hydroxytoluene. A useful chelating agent is edentate disodium.

Mixtures of two or more of any suitable excipients may be used.

Aside from topical application to treat diseases affecting the eye including glaucoma, pharmaceutical compositions containing at least one compound of formula (I) can also be administered periocularly, intraocularly, or by other effective means available in the art.

Persons skilled in the art would readily understand that a drug containing one or more of the compounds disclosed herein can be confected as a powder, pill, tablet or the like, or as a solution, emulsion, suspension, aerosol, syrup or elixir suitable for oral or parenteral administration or inhalation. For solid dosage forms or medicaments, non-toxic solid excipients for admixture with compounds disclosed herein include, but are not limited to, pharmaceutical grades of mannitol, lactose, starch, magnesium stearate, sodium saccharin, polyalkylene glycols, talcum, cellulose, glucose, sucrose, and magnesium carbonate. The solid dosage forms may be coated by a material such as glyceryl monostearate or glyceryl distearate, which is utilized in known techniques to delay disintegration and absorption in the gastrointestinal tract for the purpose of providing a sustained action over a longer period. Solid dosage forms may also be coated by the techniques described in U.S. Pat. Nos. 4,256,108, 4,166,452 and 4,265,874 to form osmotic therapeutic tablets for control release.

Pharmaceutically administrable liquid dosage forms can, for example, comprise a solution or suspension of at least one of the compounds disclosed herein and optional pharmaceutical adjutants in a carrier, such as water, saline, aqueous dextrose, glycerol, ethanol and the like. The liquid dosage forms may also contain nontoxic auxiliary substances such as wetting or emulsifying agents, pH buffering agents and the like. Examples of such auxiliary agents include sodium acetate, sorbitan monolaurate, triethanolamine, sodium acetate, triethanolamine oleate, etc. Methods for preparing such dosage forms are well-known to persons skilled in the art (see, for example, Remington's Pharmaceutical Sciences, Mack Publishing Company, Easton, Pa., 16$^{th}$ Edition, 1980).

Parenteral administration is generally characterized by subcutaneous, intramuscular, or intravenous injection. Injectables can be prepared as liquid solutions or suspensions, solid forms that can be reconstituted into solutions or suspensions prior to injection, or as emulsions. Suitable excipients include water, saline dextrose, glycerol, ethanol and the like. Such injectable pharmaceutical compositions may also contain minor amounts of non-toxic auxiliary substances such as wetting or emulsifying agents, pH buffers and the like.

Examples mentioned herein are not intended to limit the scope of the invention in any way.

The synthetic scheme set forth below, illustrates how compounds according to the invention can be made. Those skilled in the art will be able to routinely modify and/or adapt the following scheme to synthesize any compounds of the invention covered by Formula I.

General scheme

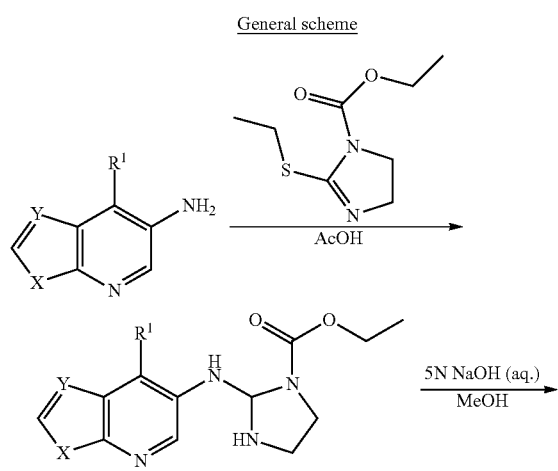

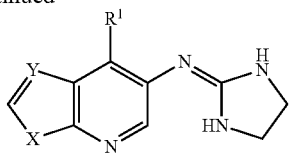

Formula I

OR

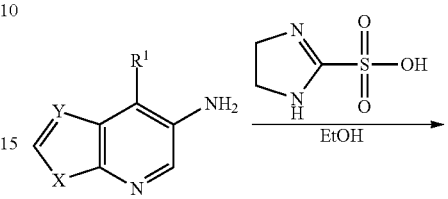

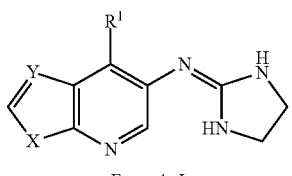

Formula I

In the first procedure, the synthesis of compounds of Formula I was started with a pyridine-3-amine derivative, which was reacted with ethyl 2-(ethylthio)-4,5-dihydro-1H-imidazole-1-carboxylate (CAS 86366-45-2) followed by removal of the protection group using 5N sodium hydroxide in methanol to afford the desired compound of Formula I.

In the second procedure, the synthesis of compounds of Formula I was started with a pyridine-3-amine derivative, which was reacted with 4,5-dihydro-1H-imidazole-2-sulfonic acid (CAS 64205-92-1) in microwave using ethanol as a solvent to afford the desired compound of Formula I.

The following examples are for illustrative purposes only and are not intended, nor should they be construed as limiting the invention in any manner. Those skilled in the art will appreciate that variations and modifications of the following examples can be made without exceeding the spirit or scope of the invention.

The IUPAC names of the compounds mentioned in the examples were generated with ACD version 8.

Unless specified otherwise in the examples, characterization of the compounds is performed according to the following methods:

NMR spectra are recorded on 300 MHz Varian and acquired at room temperature. Chemical shifts are given in ppm referenced either to internal TMS or to the residual solvent signal.

All the reagents, solvents, catalysts for which the synthesis is not described are purchased from chemical vendors such as Sigma Aldrich, Fluka, Lancaster, however some known reaction intermediates, for which the CAS registry number is mentioned, were prepared in-house following known procedures.

Usually the compounds of the invention were purified by flash column chromatography.

The following abbreviations are used in the examples:
DCM dichloromethane
EtOH ethanol
MeOH methanol
NH$_3$ ammonia
NaOH sodium hydroxide
MgSO$_4$ magnesium sulfate EtOAc ethylacetate
MPLC medium pressure liquid chromatography
DMF dimethylformamide
THF tetrahydrofuran
Na$_2$CO$_3$ sodium carbonate
PdCl$_2$(PPh$_3$)$_2$    Bis(triphenylphosphine)palladium(II) dichloride
Pd/C palladium on carbon

EXAMPLE 1

Intermediate 1

4-Methyl-1-(phenylsulfonyl)-1H-pyrrolo[2,3-b]pyridine

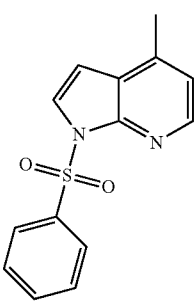 [SMILES: Cc1ccnc2c1ccn2S(=O)(=O)c1ccccc1]

A solution of 4-Bromo-1-(phenylsulfonyl)-1H-pyrrolo[2,3-b]pyridine (CAS 889939-25-7) (1.54 g, 4.56 mmol) in DMF (20 mL) was added to tetra-methylstannane (1.65 g, 9.22 mmol) followed by PdCl$_2$(PPh$_3$)$_2$ (328 mg) under argon at room temperature. The reaction mixture was stirred at 150° C. for overnight. Silica gel was added and the mixture was concentrated and purified by silica gel column chromatography using hexane:EtOAc (3:1) and gave Intermediate 1 (1.2 g, 97% yield) as a pale yellow solid.

EXAMPLE 2

Intermediate 2

4-Methyl-5-nitro-1-(phenylsulfonyl)-1H-pyrrolo[2,3-b]pyridine

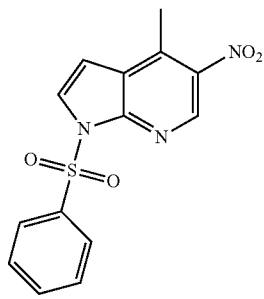 [SMILES: Cc1c([N+](=O)[O-])cnc2c1ccn2S(=O)(=O)c1ccccc1]

To a solution of tetrabutylammonium nitrate (2.48 g, 8.0 mmol) in dichloromethane (30 mL) was added trifluoroacetic anhydride (1.68 g, 8.0 mmol) at 0° C. under argon. Then Intermediate 1 (1.2 g, 4.42 mmol) in anhydrous dichloromethane (20 mL) was added slowly to the above reaction mixture at 0° C. The mixture was stirred at 0° C. for 1.5 h. The reaction was quenched with water and extracted in dichloromethane. The dichloromethane layer was dried over MgSO$_4$ and filtered, concentrated and purified by MPLC (solid load) using hexane:EtOAc (8:2) and gave Intermediate 2.

EXAMPLE 3

Intermediate 3

4-Methyl-1-(phenylsulfonyl)-1H-pyrrolo[2,3-b]pyridin-5-amine

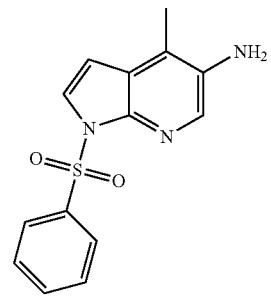 [SMILES: Cc1c(N)cnc2c1ccn2S(=O)(=O)c1ccccc1]

A mixture of Intermediate 2 (410 mg, 1.29 mmol) in THF (15 mL) and EtOH (10 mL) was added to 10% palladium on carbon (10 wt % of Pd/C; 45 mg) under argon. The mixture was hydrogenated using hydrogen balloon at room temperature for 16 hours. The reaction mixture was flushed with nitrogen and filtered through a plug of Celite® and concentrated in vacuo. The crude material was purified by flash column chromatography on silica gel using hexane:EtOAc (4:6) and gave Intermediate 3 (370 mg).

EXAMPLE 4

Intermediate 4

Ethyl 2-((4-methyl-1-(phenylsulfonyl)-1H-pyrrolo[2,3-b]pyridin-5-yl)amino)-4,5-dihydro-1H-imidazole-1-carboxylate

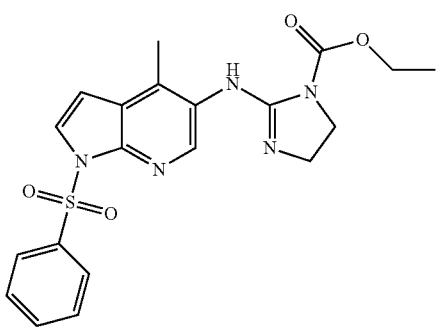 [SMILES: CCOC(=O)N1CCN=C1Nc1cnc2c(ccn2S(=O)(=O)c2ccccc2)c1C]

A solution of Intermediate 3 (390 mg, 1.25 mmol) and 1H-Imidazole-1-carboxylic acid, 2-(ethylthio)-4,5-dihydro-, ethyl ester (CAS 86366-45-2) 384 mg, 1.9 mmol) in acetic acid (8 mL) were heated at 90° C. for overnight. The mixture was concentrated and the residue was diluted with water quenched with aq. Na$_2$CO$_3$ ; a grey solid precipitated. The solid was filtered and washed with water and gave Intermediate 4 (380 mg, 66%) as a grey solid.

EXAMPLE 5

Intermediate 5

2-((4-Methyl-1-(phenylsulfonyl)-1H-pyrrolo[2,3-b]pyridin-5-yl)amino)-4,5-dihydro-1H-imidazole

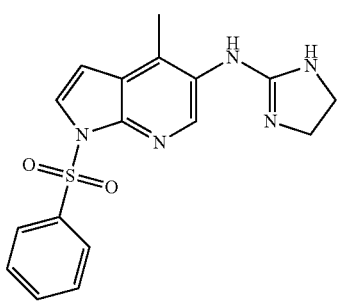 [SMILES: Cc1c(NC2=NCCN2)cnc2c1ccn2S(=O)(=O)c1ccccc1]

A solution of Intermediate 4 (390 mg, 1.25 mmol) and ethyl 2-(ethylthio)-4,5-dihydro-1H-imidazole-1-carboxylate (CAS 86366-45-2) (384 mg, 1.9 mmol) in acetic acid (8 mL) were heated at 90° C. for overnight. After concentration, the residue was diluted with water, quenched with aq. Na$_2$CO$_3$ a grey solid precipitated. The solid was filtered and washed with water gave Intermediate 5 (380 mg, 66%) as a gray solid.

EXAMPLE 6

Compound 1

N-(4,5-dihydro-1H-imidazol-2-yl)-4-methyl-1H-pyrrolo[2,3-b]pyridin-5-amine

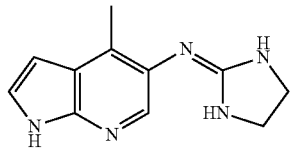 [SMILES: Cc1c(N=C2NCCN2)cnc2[nH]ccc12]

To a mixture of Intermediate 5 (380 mg, 0.89 mmol) in MeOH (10 mL) was added 5N aq. solution of NaOH (1.5 mL) and the mixture was heated at 80° C. for 4 h. Once cooled to room temperature a white solid precipitate formed, which was filtered off. Silica gel was added to the filtrate and concentrated. This material was purified by MPLC using an amine column with 10% MeOH:DCM and gave Compound 1 (26 mg).

$^1$H NMR (methanol-d$_4$) δ: 7.77 (s, 1H), 7.27 (d, J=3.2 Hz, 1H), 6.45 (d, J=3.5 Hz, 1H), 3.46 (s, 4H), 2.39 (s, 3H).

Compounds 2, 3 and 4 were prepared in a similar manner to the method described in Example 6 for Compound 1. The used starting materials and the results are tabulated below in Table 1 for each case.

TABLE 1

| Compound number | IUPAC name | Starting material | $^1$NMR (Solvent; δ ppm) |
|---|---|---|---|
| 2 | 4-Chloro-N-(imidazolidin-2-ylidene)-1H-pyrrolo[2,3-b]pyridin-5-amine | 4-chloro-1H-Pyrrolo[2,3-b]pyridin-5-amine CAS 930293-37-1 | $^1$H NMR (methanol-d$_4$) δ: 7.87 (s, 1H), 7.35 (d, J = 3.5 Hz, 1H), 6.46 (d, J = 3.2 Hz, 1H), 3.48 (s, 4H) |
| 3 | 4-Bromo-N-(imidazolidin-2-ylidene)-1H-pyrrolo[2,3-b]pyridin-5-amine | 4-bromo-1-(phenylsulfonyl)-1H-pyrrolo[2,3-b]pyridine (CAS 889939-25-7) | $^1$H NMR (methanol-d$_4$) δ: 7.85 (s, 1H), 7.37 (d, J = 3.5 Hz, 1H), 6.41 (d, J = 3.2 Hz, 1H), 3.48 (s, 4H) |
| 4 | N-(imidazolidin-2-ylidene)-1-methyl-1H-pyrrolo[2,3-b]pyridin-5-amine | 1-methyl-1H-Pyrrolo[2,3-b]pyridin-5-amine (CAS 883986-76-3) | $^1$H NMR (methanol-d$_4$) δ: 7.94 (d, J = 2.3 Hz, 1H), 7.59 (d, J = 2.3 Hz, 1H), 7.28 (d, J = 3.5 Hz, 1H), 6.37 (d, J = 3.5 Hz, 1H), 3.81 (s, 3H), 3.50 (s, 4H) |

TABLE 1-continued

| Compound number | IUPAC name | Starting material | $^1$NMR (Solvent; δ ppm) |
|---|---|---|---|
| 5 | N-(imidazolidin-2-ylidene)furo[2,3-b]pyridin-5-amine 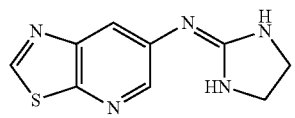 [SMILES: c1nc2cc(N=C3NCCN3)cnc2s1] | Furo[2,3-b]pyridin-5-amine (CAS 34668-30-9) | $^1$H NMR (methanol-d$_4$) δ: 7.87 (d, J = 2.3 Hz, 2H), 7.79 (d, J = 2.3 Hz, 1H), 7.64 (d, J = 2.6 Hz, 1H), 6.82 (d, J = 2.3 Hz, 1H), 3.48 (s, 4H) |

EXAMPLE 7

Compound 6

N-(4,5-dihydro-1H-imidazol-2-yl)thiazolo[5,4-b]pyridin-6-amine

A mixture of thiazolo[5,4-b]pyridin-6-amine (CAS 948306-28-3) (200 mg, 1.3 mmol) and 4,5-dihydro-1H-imidazole-2-sulfonic acid (298 mg, 1.98 mmol) in EtOH (5 mL) was heated in microwave at 150° C. for 40 min. The mixture was evaporated under reduced pressure. This material was purified by chromatography on silica gel with 5% NH$_3$-MeOH:DCM and gave (40 mg, 30% on the basis of recovered starting material) Compound 6.

$^1$H NMR (Methanol-d$_4$) δ: 9.28 (s, 1H), 8.30 (d, J=2.1 Hz, 1H), 7.95 (d, J=2.1 Hz, 1H), 3.52 (s, 4H), 3.47 (s, 1H), 3.27-3.37 (m, 3H).

Compounds 7 and 8 of the invention were prepared according to the procedure described in Example 7 for Compound 6, starting with the corresponding amino pyridine derivative, which is commercially available. The results are tabulated below in Table 2.

TABLE 2

| Compound number | IUPAC name | $^1$NMR (Solvent; δ ppm) |
|---|---|---|
| 7 | N-(imidazolidin-2-ylidene)-1H-pyrrolo[2,3-b]pyridin-5-amine | $^1$H NMR (Methanol-d$_4$) δ: 7.95 (d, J = 2.1 Hz, 5H), 7.69 (d, J = 2.1 Hz, 1H), 7.36 (d, J = 3.5 Hz, 1H), 6.42 (d, J = 3.5 Hz, 1H), 3.55 (s, 4H) |
| 8 | N-(imidazolidin-2-ylidene)-3H-imidazo[4,5-b]pyridin-6-amine | $^1$H NMR (Methanol-d$_4$) δ: 8.50 (s, 1H), 8.38 (d, J = 2.3 Hz, 1H), 8.05 (d, J = 2.3 Hz, 1H), 3.80 (s, 4H) |

The following assays and animal models are used to demonstrate the potency and selectivity of the compounds according to the invention.

EXAMPLE 8

RSAT Compound Screening

The novel compounds of the invention were synthesized and tested for alpha adrenergic activity using the Receptor Selection and Amplification Technology (RSAT) assay (Messier et. al., 1995, Pharmacol. Toxicol. 76, pp. 308-311). Cells expressing each of the alpha 2 adrenergic receptors alone were incubated with the various compounds and a receptor-mediated growth response was measured. The compound's activity is expressed as its relative efficacy compared to a standard full agonist (see Table 3). The compounds of this invention activate alpha 2 receptors.

TABLE 3

Biological Data: Intrinsic Activity EC$_{50}$ nM (efficacy)

| Compound number | IUPAC name | Alpha 2B | Alpha 2C | Alpha 2A |
|---|---|---|---|---|
| 1 | N-(4,5-dihydro-1H-imidazol-2-yl)-4-methyl-1H-pyrrolo[2,3-b]pyridin-5-amine | potent (0.82) | potent (0.94) | 8.2 (0.85) |
| 2 | 4-Chloro-N-(imidazolidin-2-ylidene)-1H-pyrrolo[2,3-b]pyridin-5-amine | 5.36 (0.72) | 10.5 (0.91) | 25.2 (0.73) |
| 3 | 4-Bromo-N-(imidazolidin-2-ylidene)-1H-pyrrolo[2,3-b]pyridin-5-amine | 32.6 (0.17) | 31.2 (0.84) | 62.2 (0.16) |
| 4 | N-(imidazolidin-2-ylidene)-1-methyl-1H-pyrrolo[2,3-b]pyridin-5-amine | 114 (0.57) | 31 (0.93) | NA |

TABLE 3-continued

Biological Data: Intrinsic Activity EC$_{50}$ nM (efficacy)

| Compound number | IUPAC name | Alpha 2B | Alpha 2C | Alpha 2A |
|---|---|---|---|---|
| 5 | N-(imidazolidin-2-ylidene)furo[2,3-b]pyridin-5-amine | NA | 2107 (0.73) | NA |
| 6 | N-(4,5-dihydro-1H-imidazol-2-yl)thiazolo[5,4-b]pyridin-6-amine | 267 (0.46) | 10 (0.97) | NA |
| 7 | N-(imidazolidin-2-ylidene)-1H-pyrrolo[2,3-b]pyridin-5-amine | potent (0.87) | 7.3 (0.94) | 16.2 (0.89) |
| 8 | N-(imidazolidin-2-ylidene)-3H-imidazo[4,5-b]pyridin-6-amine | 722 (0.61) | 448 (0.87) | NA |

NA = not active

What is claimed is:

1. A method of treating a condition associated with the alpha 2 adrenergic receptors, wherein the condition is a skin condition selected from: rosacea, sunburn, psoriasis, acne rosacea, menopause-associated hot flashes, hot flashes resulting from orchiectomyatopic dermatitis, photoaging, seborrheic dermatitis, acne, allergic dermatitis, redness of the skin, telangiectasia of the face, rhinophyma, red bulbous nose, acne-like skin eruptions, burning or stinging sensation of the face, erythema of the skin, cutaneous hyperactivity with dilation of blood vessels of the skin, Lyell's syndrome, Stevens-Johnson syndrome, erythema multiforme minor and erythema multiforme major, which comprises administering to a mammal in need thereof a pharmaceutical composition comprising a therapeutically effective amount of at least one compound of Formula I:

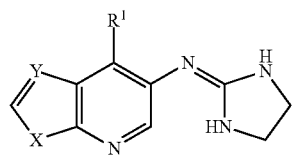

Formula I wherein:
$R^1$ is hydrogen, $C_{1-8}$ alkyl or halogen;
Y is CH or N;
X is O, S or NR; and
R is H or $C_{1-3}$ alkyl.

2. An article of manufacture comprising packaging material and a pharmaceutical agent contained within said packaging material, wherein the pharmaceutical agent is therapeutically effective and wherein the packaging material comprises a label which indicates the pharmaceutical agent can be used for treating a condition associated with the alpha 2 adrenergic receptors, wherein the condition is a skin condition selected from: rosacea, sunburn, psoriasis, acne rosacea, menopause-associated hot flashes, hot flashes resulting from orchiectomyatopic dermatitis, photoaging, seborrheic dermatitis, acne, allergic dermatitis, redness of the skin, telangiectasia of the face, rhinophyma, red bulbous nose, acne-like skin eruptions, burning or stinging sensation of the face, erythema of the skin, cutaneous hyperactivity with dilation of blood vessels of the skin, Lyell's syndrome, Stevens-Johnson syndrome, erythema multiforme minor and erythema multiforme major, and wherein said pharmaceutical agent comprises an effective amount of at least one compound of Formula I:

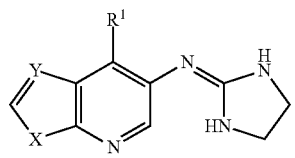

Formula I wherein:
$R^1$ is hydrogen, $C_{1-8}$ alkyl or halogen;
Y is CH or N;
X is O, S or NR; and
R is H or $C_{1-3}$ alkyl.

3. The method according to claim 1, wherein:
$R^1$ is hydrogen, methyl, bromine or chlorine;
Y is CH or N;
X is O, S or NR; and
R is hydrogen or methyl.

4. The method according to claim 1, wherein:
$R^1$ is hydrogen;
Y is CH;
X is O or NR; and
R is hydrogen or methyl.

5. The method according to claim 1, wherein:
$R^1$ is methyl;
Y is CH;
X is NR; and
R is methyl.

6. The method according to claim 1, wherein:
$R^1$ is bromine or chlorine;
Y is CH;
X is NR; and
R is hydrogen.

7. The method according to claim 1, wherein:
$R^1$ is hydrogen;
Y is N;
X is O, S or NR; and
R is hydrogen or methyl.

8. The method according to claim 1, wherein the compound is selected from:
- N-(imidazolidin-2-ylidene)-1H-pyrrolo[2,3-b]pyridin-5-amine;
- N-(imidazolidin-2-ylidene)-4-methyl-1H-pyrrolo[2,3-b]pyridin-5-amine;
- 4-Chloro-N-(imidazolidin-2-ylidene)-1H-pyrrolo[2,3-b]pyridin-5-amine;
- 4-Bromo-N-(imidazolidin-2-ylidene)-1H-pyrrolo[2,3-b]pyridin-5-amine;
- N-(imidazolidin-2-ylidene)-1-methyl-1H-pyrrolo[2,3-b]pyridin-5-amine;
- N-(imidazolidin-2-ylidene)furo[2,3-b]pyridin-5-amine;
- N-(imidazolidin-2-ylidene)-3H-imidazo[4,5-b]pyridin-6-amine; and
- N-(imidazolidin-2-ylidene)thiazolo[5,4-b]pyridin-6-amine.

9. The method according to claim 1, wherein the mammal is a human.

\* \* \* \* \*